United States Patent [19]

Mabuchi et al.

[11] 4,123,616

[45] Oct. 31, 1978

[54] PROCESS FOR HYDROGENATION OF ORGANIC PEROXIDE

[75] Inventors: Shunsuke Mabuchi; Kenji Tsuzuki; Sadakatsu Kumoi, all of Shin-nanyo, Japan

[73] Assignee: Toyo Soda Manufacturing Co., Ltd., Yamaguchi, Japan

[21] Appl. No.: 806,703

[22] Filed: Jun. 15, 1977

[30] Foreign Application Priority Data

Jul. 15, 1976 [JP] Japan .................................. 51-83513

[51] Int. Cl.$^2$ ............................................. C07C 29/00
[52] U.S. Cl. ...................................... 568/861; 568/840
[58] Field of Search ...................... 260/635 P, 632 R; 568/861, 840

[56] References Cited

U.S. PATENT DOCUMENTS

| | | | |
|---|---|---|---|
| 2,421,451 | 6/1947 | Balcar | 260/635 A |
| 2,879,306 | 3/1959 | Hutchinson | 260/635 R |
| 3,565,921 | 2/1971 | Gobron et al. | 260/632 R |
| 3,896,051 | 7/1975 | Mabuchi et al. | 260/635 R |
| 3,914,295 | 10/1975 | Rosenthall et al. | 260/632 R |
| 4,002,692 | 1/1977 | Mabuchi et al. | 260/635 R |

*Primary Examiner*—Joseph E. Evans
*Attorney, Agent, or Firm*—Oblon, Fisher, Spivak, McClelland & Maier

[57] ABSTRACT

An organic peroxide is hydrogenated to produce the corresponding mono- or polyhydric alcohol in a suspensoid process or a fluidized bed process in the presence of more than 3 wt. % of a nickel catalyst at a reaction temperature of 140° to 200° C under a hydrogen pressure of 10 to 300 Kg/cm$^2$ by feeding the organic peroxide at a rate of 0.05 to 10 g/hr. per 1 g of the nickel catalyst.

11 Claims, No Drawings

PROCESS FOR HYDROGENATION OF ORGANIC PEROXIDE

BACKGROUND OF THE INVENTION

1. Field of the Invention

The present invention relates to a process for hydrogenation of an organic peroxide to produce a mono- or polyhydric alcohol with a nickel catalyst wherein the catalytic activity of the nickel catalyst is maintained by improving the conditions under which the nickel catalyst contacts the organic peroxide.

2. Description of the Prior Art

It has been known that a mono- or polyhydric alcohol corresponding to an organic peroxide can be produced by contacting the organic peroxide with hydrogen in the presence of a neutral hydrogenation catalyst.

In the industrial operation of the reaction, the following two serious problems are encountered. One is the danger of explosion of the organic peroxide and the other is the poisoning of the hydrogenation catalyst. The present invention is concerned with preventing the poisoning of the catalyst.

Maintaining the catalytic activity of a nickel catalyst during the hydrogenation of an organic peroxide has been considered difficult because the poisoning of the nickel catalyst by the organic peroxide is very high. The severe poisoning of the nickel catalyst is clearly understood by the description of Example 3 of U.S. Pat. No. 2,879,306 wherein polymeric butadiene peroxide, an alternant copolymer of butadiene and oxygen, is hydrogenated to produce 1,2-butanediol and 1,4-butanediol. In order to hydrogenate only 6.5 g of polymeric butadiene peroxide, 0.5 g of Raney nickel catalyst (corresponding to 7.7 wt. % relative to the polymeric butadiene peroxide) is used in the first reaction step. It is shown that the catalytic activity of the Raney nickel is substantially lost just by using it in one partial hydrogenation.

Attempts have been made to reactivate the poisoned nickel catalyst used for the production of the corresponding mono- or polyhydric alcohol by contacting an organic peroxide with hydrogen in the presence of the nickel catalyst. (U.S. Pat. No. 3,896,051 and British Pat. No. 1,400,340). The properties of the catalyst poison in the hydrogenation of organic peroxides with nickel catalyst have been studied in the prior art.

The inventors have studied this process and found that in the hydrogenation of organic peroxides with a nickel catalyst, the poisoned nickel catalyst can be reactivated by contacting the catalyst with hydrogen at 140° to 250° C. in an oxygen-containing polar organic solvent which is resistant to hydrogenation. The inventors have further found that a suitable solvent for use in the reactivation is the reaction mixture resulting from hydrogenation of the organic peroxide. That is, it has been found that when an organic peroxide is contacted with hydrogen in the presence of a nickel catalyst to produce the corresponding mono- or polyhydric alcohol, the activity of the catalyst can be maintained for a long period of time by providing additional reaction time for reactivation of the poisoned catalyst after the point where no further increase in yield of the alcohol is observed, indicating the completion of the hydrogenation of the organic peroxide. The present invention has resulted from these discoveries and is not simply a specification of reaction conditions which are obvious over a conventional consideration to use a long reaction time for the hydrogenation of organic peroxides. In any event, it has not been known to be industrially advantageous to prolong the reaction after its completion, since the catalytic activity of the nickel catalyst can not be maintained for a long period of time solely by prolonging the reaction time if other essential conditions are not met.

The inventors have studied the poisoning of nickel catalysts used for the hydrogenation of organic peroxides to produce the corresponding mono- or polyhydric alcohols, and have found a novel process for hydrogenation of organic peroxides which is quite different from other processes for hydrogenation of compounds having carbonyl groups or unsaturated bonds.

SUMMARY OF THE INVENTION

Accordingly, it is an object of the present invention to provide a process for hydrogenation of an organic peroxide to produce the corresponding mono- or polyhydric alcohol wherein the catalytic activity of the nickel catalyst is maintained for a long period of time.

Briefly, the foregoing and other objects of the present invention can be attained by providing an hydrogenation of an organic peroxide to produce the corresponding mono- or polyhydric alcohol in a suspensoid process or a fluidized bed process in the presence of more than 3 wt. % of a nickel catalyst, at a reaction temperature of 140° to 200° C., under a hydrogen pressure of 10 l to 300 Kg/cm$^2$ by feeding the organic peroxide at a rate of 0.05 to 10 g/hr. per 1 g of the nickel catalyst.

DETAILED DESCRIPTION OF THE PREFERRED EMBODIMENTS

Suitable nickel catalysts used in the present invention include pure nickel, Raney nickel, nickel catalysts obtained by the thermal decomposition of organic acid salts such as nickel formate, and carrier supported nickel catalysts supported on diatomaceous earth, alumina, pumice zeolite or basic carriers; Raney multicomponent alloy catalysts containing more than 50% of nickel obtained by forming a three- or four-component alloy by blending nickel-aluminum alloy with another metal or other metals including Fe,Cr,Mo,W,Mn,Co,-Cu,Sn and the like and developing the alloy; or a nickel-rhenium catalyst.

Suitable such nickel catalysts include those having an average particle diameter less than 300μm, preferably from 10 to 200 μm; a surface area greater than 30 m$^2$/g, preferably from 50 to 200 m$^2$/g; and a nickel content greater than 20 wt. %, preferably from 30 to 95 wt. %. The carriers for and the manner of preparation of the nickel catalysts are not critical. However, the nickel catalyst should have fluidity in the hydrogenation reactor.

Suitable organic peroxides used in the present invention include peroxides of conjugated diolefins such as 1,3-butadiene, isoprene, 2,5-dimethyl-2,4-hexadiene or alkyl substituted conjugated dienes; peroxides of cyclic conjugated diolefins such as cyclopentadiene, cyclohexadiene, furan or alkyl substituted cyclic conjugated diolefins; polymeric olefinic peroxides such as an alternant copolymer of oxygen and indene or styrene and the like; other polymeric peroxides; monomeric dialkylperoxides such as 1,2-dioxane, 1,4-peroxybutene-2, 2,7-peroxy-2,6-dimethyloctadiene-3,5 and hydroperoxides such as 2-hydroperoxytetrahydrofuran, n-butyl hydroperoxide and the like.

The organic peroxide can be added as an inert solvent solution having a peroxide concentration of 10 to 50 wt. %. Suitable inert solvents include the cyclic ethers, such as tetrahydrofuran, tetrahydropyran, dioxan, the saturated carboxylic acid esters, such as ethyl acetate, methyl propionate.

The present invention will be illustrated for the hydrogenation of polymeric butadiene peroxide.

In the process of the present invention, the nickel catalyst is suspended in a solvent such as ethyl acetate, hydrogen is introduced at a pressure of 10 to 300 Kg-cm$^2$, a mixture of the polymeric butadiene peroxide diluted to 20 to 35 wt. % with ethyl acetate is added to the suspension of the catalyst in an amount sufficient to react it using more than 3 wt. % of the nickel catalyst, the reaction temperature is 140° to 200° C., and the polymeric butadiene peroxide is added at a rate of 0.05 to 10 g/hr. per 1 g of the nickel catalyst.

From the standpoint of catalyst durability, it is preferred that the concentration of the catalyst be high, but it is critical to maintain the fluidity of the catalyst. Accordingly, the concentration of the catalyst should be in the range of 3 to 70 wt. %. It is possible to use it in higher concentrations when the bulk density is high as is the case for Raney nickel. When the concentration of the catalyst is given by weight percent, the weight of the catalyst includes the carrier and other metal components together with the nickel metal. The reaction can be carried out using the semicontinuous or the continuous method. The concentration of the catalyst is very high, and thus it is preferable to retain the catalyst in the reactor. The concentration of the catalyst in conventional hydrogenations using suspended nickel catalyst is usually lower than 3 wt. % in industrial processes. Although it is expected that the reaction can just as well be performed using a high concentration of the nickel catalyst as a low concentration no advantageous effect is expected by increasing the concentration of the nickel catalyst in the conventional processes. However, in the hydrogenation of organic peroxides, it has unexpectedly been found possible to maintain catalytic activity for longer times by using the nickel catalyst suspension in high concentration.

When the reaction temperature is lower than 140° C., the reactivation rate of the poisoned catalyst is too low and consequently the catalytic activity cannot be maintained for long periods of time. It is preferred that the organic peroxide be fed into the suspension of the catalyst at a temperature higher than 140° C. without any contact of the two at less than 140° C. When the reaction temperature is higher than 200° C., the yield of the object alcohol is too low. The rate of addition of the organic peroxide should be in the range of 0.05 to 10 g/hr. per 1 g of the nickel catalyst, which rate is substantially lower than the rate of hydrogenation. However, this is the condition required for preventing loss of catalytic activity of the catalyst. From the standpoint of catalyst life, the rate of addition of organic peroxide should preferably be slow.

The reaction mechanism for reactivation of the poisoned nickel catalyst has not been clearly delineated. In the process of the present invention, the rate at which the nickel catalyst is poisoned by the organic peroxide is not permitted to exceed its rate of reactivation by contact with hydrogen in the reaction mixture of the oxygen-containing polar organic solvent, such that the catalyst can be maintained at about its initial activity. In a suspension having more than 3 wt. % of highly active catalyst, hydrogenation of the organic peroxide is virtually instantaneous, and consequently the thermal decomposition of the organic peroxide with attendant permanent poisoning of the nickel catalyst, as well as other side reactions, can be greatly decreased.

The hypothesis that hydrogenation of the organic peroxide is virtually instantaneous is based on the following facts. Polymeric butadiene peroxide is thermally decomposed gradually at 100° C., rapidly at 120° C., and explosively at 140° C. When the thermally decomposed product of polymeric butadiene peroxide is hydrogenated, 1,2-butanediol and 1,4-butanediol are not formed in substantial amounts. However, in accordance with the process of the present invention, 1,2-butanediol and 1,4-butanediol can be obtained in high yield.

The hypothesis of immediate hydrogenation has been confirmed by a study of the hydrogenation rate. If the organic peroxide is not immediately hydrogenated, permanent poisoning of the nickel catalyst is caused by the thermal decomposition products of the organic peroxide. This permanent poisoning of the nickel catalyst becomes more severe with more incomplete hydrogenation of the organic peroxide. The inactivated catalyst poisoned as a result of incomplete hydrogenation can not be reactivated even though the reaction time is prolonged. Accordingly, the method and apparatus for introducing the organic peroxide should be designed so as to prevent the thermal decomposition of the organic peroxide as far as possible by rapidly contacting the organic peroxide with a suspension of the highly active nickel catalyst in high concentration and under sufficient hydrogen pressure.

The durability of the catalyst is raised by increasing the hydrogen pressure and the pressure is usually in the range 10 to 300 Kg/cm$^2$.

Heretofore, it had been thought that the catalytic activity of nickel catalysts cannot be maintained for a long time in the hydrogenation of organic peroxides since the poisoning is severe. However, in accordance with the process of the present invention, the catalytic activity of the nickel catalyst can be maintained, as it can be in the hydrogenation of compounds having carbonyl groups or unsaturated bonds. The key feature of the present invention is that it permits hydrogenation of organic peroxides to produce mono- or polyhydric alcohols in one step.

Having generally described the invention, a more complete understanding can be obtained by reference to certain specific examples, which are included for purposes of illustration only and are not intended to be limiting unless otherwise specified.

EXAMPLE 1

In a continuous oxidizing reactor consisting of a stainless steel (SUS-32) 2 liter autoclave having an inner diameter of 95 mm, a height of 300 mm and a compressive strength of 100 Kg/cm$^2$, and equipped with an electromagnetic stirrer, butadiene was oxidized in a solvent of ethyl acetate at 90° C. under 1 Kg/cm$^2$ of oxygen partial pressure and 10 Kg/cm$^2$ of nitrogen partial pressure to obtain a butadiene conversion of 30% as a 20 wt. % solution of polymeric butadiene peroxide in ethyl acetate. The reaction mixture was concentrated to 33.3 wt. % by removing the unreacted butadiene by distillation under reduced pressure. The product was used for the hydrogenation.

In the hydrogenation, 15 g of a nickel catalyst which is resistant to sulfur (manufactured by Nikki Kagaku K.K.) and 50 g of ethyl acetate were charged into a 200 cc stainless steel (SUS-32) autoclave equipped with an electromagnetic stirrer, and 60 g of an ethyl acetate solution containing 20 g of the polymeric butadiene peroxide were added over 4 hours by a microvolumetric pump, under 100 Kg/cm² of hydrogen pressure, at 150° C.

The polymeric butadiene peroxide was fed into the suspension of catalyst, with stirring, through an inlet pipe having an inner diameter of 1 mm, an outer diameter of 5 mm, and a length of 10 mm, and which was connected to the cover of the autoclave. The temperature of the thermometer pipe at a distance of 10 mm from the cover was 91° C. Accordingly, the temperature of the polymeric butadiene peroxide at the time of addition was about 90° C.

After charging with the polymeric butadiene peroxide, the autoclave was cooled to lower the reaction temperature to room temperature. The catalyst was separated and the reaction product was analyzed by gas chromatography.

The resulting yields of 1,4-butanediol and 1,2-butanediol, based on the polymeric butadiene peroxide, were 53.5% and 25.1%, respectively.

The separated catalyst was used for further hydrogenation of polymeric butadiene peroxide without any reactivation.

The operation was repeated 60 times without decrease in the yields of 1,4-butanediol and 1,2-butanediol.

The nickel catalyst which is resistant to sulfur (Nikki Kagaku K.K.) has the following formula:

| Ni | 45 to 47% |
|---|---|
| Cr | 2 to 3% |
| Cu | 2 to 3% |
| Diatomaceous earth | 27 to 29% |
| Graphite | 4 to 5% |
| Type of Ni | Ni + NiO |

REFERENCE EXAMPLE 1

In the reactor of Example 1, 10 g of the nickel catalyst and 50 g of ethyl acetate were charged, and then 60 g of an ethyl acetate solution containing 20 g of polymeric butadiene peroxide was added over 4 hours by a microvolumetric pump, under 50 Kg/cm² of hydrogen pressure at 70° C., after which the reaction temperature was raised to 150° C. during 30 minutes, while maintaining 50 Kg/cm² of hydrogen pressure, and the hydrogenation was continued for 30 minutes.

After reaction, the nickel catalyst was separated and the reaction mixture was analyzed by gas chromatography. The yields of 1,2-butanediol and 1,4-butanediol were measured.

The catalyst was separated and used for further hydrogenation of polymeric butadiene peroxide.

REFERENCE EXAMPLE 2

The same procedure was used as in the process of Reference Example 1 except that the solution of polymeric butadiene peroxide was added at 130° C., the temperature was raised to 150° C. during 15 minutes, after which hydrogenation of the polymeric butadiene peroxide was continued under 50 Kg/cm² of hydrogen pressure for 3 hours and 45 minutes.

EXAMPLE 2

The same procedure was used as in the process of Reference Example 1 except that polymeric butadiene peroxide was added at 150° C., and the polymeric butadiene peroxide was hydrogenated under those conditions for 4 hours.

The results are shown in Table 1.

Table 1

| Number of times the catalyst was reused | 1 | 8 | 9 | 15 | 18 | 20 | 23 | 30 |
|---|---|---|---|---|---|---|---|---|
| Reference Example 1 | | | | | | | | |
| 1,4-butanediol Yield (%) | 53.5 | 45.7 | 26.0 | — | — | — | — | — |
| 1,2-butanediol Yield (%) | 25.0 | 17.1 | 6.5 | — | — | — | — | — |
| Reference Example 2 | | | | | | | | |
| 1,4-butanediol Yield (%) | 52.9 | 52.5 | 53.0 | 51.5 | 50.2 | 46.6 | 25.1 | — |
| 1,2-butanediol Yield (%) | 25.1 | 25.1 | 24.9 | 23.4 | 21.3 | 19.8 | 5.8 | — |
| Example 2 | | | | | | | | |
| 1,4-butanediol Yield (%) | 53.3 | 53.5 | 53.7 | 53.2 | 53.5 | 53.1 | 53.5 | 53.2 |
| 1,2-butanediol Yield (%) | 24.8 | 24.9 | 24.9 | 25.1 | 24.8 | 24.9 | 25.2 | 24.9 |

From the results of Reference Examples 1 and 2, it was found that the catalyst could not be reactivated, and its life was quite short, once the hydrogenation was conducted at a temperature out of the range 140° to 200° C., even if the temperature were subsequently raised to the range 140° to 200° C.

EXAMPLE 3

In the reactor of Example 1, 3 g of Raney nickel and 45 g of tetrahydrofuran were charged, and 60 g of a tetrahydrofuran solution containing 30 g of t-butyl hydroperoxide was added over 2 hours by a microvolumetric pump, under 15 Kg/cm² of hydrogen pressure, at 180° C.

The tetrahydrofuran solution of t-butyl hydroperoxide was prepared by diluting 37.5 g of 80% t-butyl hydroperoxide with 22.5 g of tetrahydrofuran.

After the addition, the reaction temperature was lowered to room temperature and the reaction mixture was analyzed by gas chromatography.

The yield of the resulting t-butyl alcohol was quantitative.

The catalyst was separated and used for further hydrogenation of t-butyl hydroperoxide.

The operation was repeated 5 times and in the fifth operation, the yield of t-butyl alcohol was also quantitative.

EXAMPLE 4

In the reactor of Example 1, 1.5 g of the sulfur-resistant nickel catalyst, and 50 g of tetrahydrofuran were charged, and 60 g of a tetrahydrofuran solution containing 30 g of t-butyl hydroperoxide was added over 2 hours by a microvolumetric pump, under 100 Kg/cm² of hydrogen pressure, at 180° C. After the addition, the reaction temperature was lowered to room temperature.

The catalyst was separated and the reaction mixture was analyzed by gas chromatography. The resulting yield of t-butyl alcohol was quantitative.

The catalyst was separated and used for further hydrogenation of t-butyl hydroperoxide. The operation was repeated 5 times and in the fifth operation, the yield of t-butyl alcohol was also quantitative.

REFERENCE EXAMPLE 3

In a 200 cc stainless steel autoclave, equipped with an electromagnetic stirrer, 1 g of sulfur-resistant nickel catalyst, 45 g of tetrahydrofuran, and 50 g of 80% t-butyl hydroperoxide were charged, and the temperature was raised from ambient temperature to 150° C. during 30 minutes, under 15 Kg/cm$^2$ of hydrogen pressure. The temperature suddenly rose above 150° C. and an explosion resulted.

REFERENCE EXAMPLE 4

In the autoclave of Reference Example 3, 1 g of Raney nickel, 45 g of tetrahydrofuran and 50 g of 80% t-butyl hydroperoxide were charged, and the temperature was raised from room temperature to 120° C. during 1.5 hours, under 20 kg/cm$^2$ of hydrogen pressure after which the hydrogenation was conducted under these conditions for 3 hours.

The autoclave was then cooled, to lower the reaction temperature to room temperature. The catalyst was separated and the reaction mixture was analyzed. The yield of t-butyl alcohol, based on t-butyl hydroperoxide, was 21.2%.

REFERENCE EXAMPLE 5

In the autoclave of Reference Example 3, 1 g of Raney nickel, 45 g of tetrahydrofuran and 50 g of 80% t-butyl hydroperoxide were charged, and the temperature was raised from room temperature to 120° C. during 1.5 hours, under 20 Kg/cm$^2$ of hydrogen pressure, after which the hydrogenation was conducted under these conditions for 3 hours. The temperature was then raised from 120° to 180° C. during 30 minutes and the hydrogenation was continued at 180° C., under 20 Kg/cm$^2$ of hydrogen pressure, for 3 hours.

After the reaction, the autoclave was cooled to room temperature, the catalyst was separated, and the reaction mixture was analyzed by gas chromatography. The resulting yield of t-butyl alcohol, based on t-butyl hydroperoxide, was 66.5%.

EXAMPLE 5

In a 1 liter stainless steel autoclave which had 300 Kg/cm$^2$ of compressive strength and was equipped with an electromagnetic stirrer, 300 g of tetrahydrofuran and 1 g of 2-hydroperoxy tetrahydrofuran initiator were charged, and the reaction was conducted at 100° C. for 1 hour, under 1.5 Kg/cm$^2$ of oxygen partial pressure and 15 Kg/cm$^2$ of nitrogen partial pressure. The reaction mixture, which had achieved a 17% tetrahydrofuran conversion, was concentrated to 33.3 wt. % by distillation under reduced pressure. The product was used for the hydrogenation.

In the reactor of Example 1, 10 g of a modified Raney nickel catalyst containing 0.7% of Cr, and 50 g of ethyl acetate were charged. Then, 60 g of an ethyl acetate solution containing 20 g of 2-hydroperoxytetrahydrofuran was added over 3 hours by a microvolumetric pump, under 100 Kg/cm$^2$ of hydrogen pressure, at 150° C.

After the addition, the autoclave was cooled, to lower the reaction temperature to room temperature. The catalyst was separated, and the reaction mixture was analyzed by gas chromatography.

The resulting yields of 1,4-butanediol, γ-butyrolactone and tetrahydrofuran, based on 2-hydroperoxy tetrahydrofuran, were 83.7%, 7.2% and 4.1%, respectively.

The operation was repeated 60 times without a decrease in the yield of 1,4-butanediol.

EXAMPLE 6

A 25% by weight ethyl acetate solution of polymeric butadiene peroxide obtained by the process of Example 1 was used for the hydrogenation.

In a 200 cc stainless steel (SUS-32) autoclave, equipped with an electromagnetic stirrer, the inlet pipe of Example 1 for feeding the solution of polymeric butadiene peroxide, and an outlet through which the reaction mixture may be discharged by filtering through a ceramic filter (G-4), 30 g of the sulfur-resistant nickel catalyst was charged. Then, 70 g of the 25% ethyl acetate solution of polymeric butadiene peroxide was continuously added, under 100 Kg/cm$^2$ of hydrogen pressure, at 150° C., to hydrogenate it.

Additional 25% ethyl acetate solution of polymeric butadiene peroxide was added from a storage tank, at a rate of 60 g/hr., by a microvolumetric pump. The reaction mixture was simultaneously being discharged into a received under lower pressure so as to maintain a constant volume of solution in the reactor, by periodically opening an electromagnetic valve with a timer.

After a portion of the reaction mixture had discharged to the filter, a portion of the hydrogen gas in autoclave was released, thus raising the pressure in the receiver. The electromagnetic valve of the outlet was closed upon detection of the pressure increase, and the receiver was charged to a predetermined pressure.

The hydrogenation of polymeric butadiene peroxide was continuously conducted for a total of 1000 hours.

The yields of 1,4-butanediol and 1,2-butanediol at the end of the run were substantially the same as those at the outset of the reaction.

The average yields of 1,4-butanediol and 1,2-butanediol, based on polymeric butadiene peroxide, were 53.3% and 25.2%, respectively.

Having now fully described the invention, it will be apparent to one of ordinary skill in the art that many changes and modifications can be made thereto without departing from the spirit or the scope of the invention as set forth herein.

What is claimed as new and desired to be secured by letters patent of the United States is:

1. A process for hydrogenation of an organic peroxide to produce the corresponding mono- or polyhydric alcohol while substantially avoiding loss of catalyst activity for a long period of time which comprises feeding the organic peroxide into a suspension of more than 3 wt. % of a nickel catalyst in an inert solvent, at a rate of 0.05 to 10 g/hr. per 1 g of the nickel catalyst, at a reaction temperature of 140° to 200° C., under 10 to 300 Kg/cm$^2$ of hydrogen pressure, in a suspensoid process or a fluidized bed process; wherein said organic peroxide is fed into said suspension of the nickel catalyst heated at higher than 140° C. without contacting said suspension at lower than 140° C.

2. The process of claim 1 wherein the concentration of said nickel catalyst in the reaction mixture is in the range 3 to 70 wt. %.

3. The process of claim 1 wherein said organic peroxide is added as an inert solvent solution of the organic peroxide at a concentration of 10 to 50 wt.%.

4. The process of claim 1 wherein said nickel catalyst is Raney nickel catalyst, a carrier supported nickel catalyst, or a Raney multicomponent alloy catalyst obtained by developing an alloy formed by blending nickel-aluminum with another metal.

5. The process of claim 1 wherein said nickel catalyst has an average particle diameter of 10 to 300 μm in a suspension.

6. The process of claim 1 wherein said organic peroxide is an olefinic peroxide.

7. The process of claim 1 wherein said organic peroxide is an alternant copolymer of a conjugated diolefin and oxygen.

8. The process of claim 1 wherein said organic peroxide is 1,3-butadiene peroxide.

9. The process of claim 1 wherein said organic peroxide is a dialkyl peroxide.

10. The process of claim 1 wherein said organic peroxide is a hydroperoxide.

11. The process of claim 1 wherein said organic peroxide is added continuously and the reaction mixture is withdrawn at a rate such that a constant volume of solution is maintained.

* * * * *